(12) United States Patent
Sobecki et al.

(10) Patent No.: US 10,842,137 B2
(45) Date of Patent: Nov. 24, 2020

(54) SIEVING DEVICES FOR PUPAE SEPARATION

(71) Applicant: Verily Life Sciences LLC, South San Francisco, CA (US)

(72) Inventors: Robert Sobecki, Brisbane, CA (US); Charles Behling, Brisbane, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 15/990,461

(22) Filed: May 25, 2018

(65) Prior Publication Data

US 2018/0271074 A1 Sep. 27, 2018

Related U.S. Application Data

(62) Division of application No. 15/467,145, filed on Mar. 23, 2017, now Pat. No. 10,342,222.

(51) Int. Cl.
*B07B 1/46* (2006.01)
*A01K 67/033* (2006.01)

(52) U.S. Cl.
CPC .............. *A01K 67/033* (2013.01); *B07B 1/46* (2013.01); *B07B 1/469* (2013.01)

(58) Field of Classification Search
CPC .... B03B 5/00; B03B 5/28; B03B 5/40; B03B 5/64; A01K 67/033; B07B 1/46; B07B 1/4636; B07B 1/469; B07B 1/06; B07B 1/12
USPC ......... 209/17, 269, 370, 371, 397, 399, 405, 209/408, 409
See application file for complete search history.

(56) References Cited

U.S. PATENT DOCUMENTS

| 35,594 | A | * | 6/1862 | Ensign | ................. | B07B 1/4672 |
| | | | | | | 209/328 |
| 271,497 | A | | 1/1883 | McClure | | |
| 575,095 | A | | 1/1897 | Bartelt | | |

(Continued)

FOREIGN PATENT DOCUMENTS

| CN | 202070486 | 12/2011 |
| CN | 103704179 | 4/2014 |

(Continued)

OTHER PUBLICATIONS

English Translation of CN 20369226; INV: Yang et al.; Pub; Date: Jul. 2014 (Year: 2014).*

(Continued)

*Primary Examiner* — Joseph C Rodriguez
(74) *Attorney, Agent, or Firm* — Kilpatrick Townsend & Stockton LLP

(57) ABSTRACT

A sieving device is described. The sieving device includes a sieve surface attached to a sieve rim. A set of openings is formed in the sieve surface so as to define a set of pathways extending through the sieve surface. The set of opening are defined by a length dimension that is greater than a width dimension. When the sieve surface is submerged in a liquid, a first pupa having a first cephalothorax width that is less than the width dimension is free to move through any one of the set of openings, and a second pupa having a second cephalothorax width that is greater than the width dimension is prevented from moving through the set of openings.

20 Claims, 5 Drawing Sheets

(56) References Cited

U.S. PATENT DOCUMENTS

| | | | | |
|---|---|---|---|---|
| 1,468,261 | A | * | 9/1923 | Collins ............... D21F 1/66 209/250 |
| 1,595,685 | A | | 8/1926 | Terencio |
| 1,886,174 | A | * | 11/1932 | Hazeltine ............... B07B 1/00 209/269 |
| 1,989,005 | A | | 1/1935 | Ernst et al. |
| 2,135,069 | A | * | 11/1938 | Deister ............... B07B 1/284 209/382 |
| 2,861,688 | A | * | 11/1958 | Harms ............... B01D 35/28 210/744 |
| 3,194,397 | A | | 7/1965 | Gunter |
| 3,223,237 | A | | 12/1965 | Harrod, Jr. et al. |
| 3,334,750 | A | | 8/1967 | Ullman, Jr. |
| 3,363,769 | A | * | 1/1968 | Wilmot ............... B01D 29/945 210/251 |
| 3,696,788 | A | | 10/1972 | Day et al. |
| 3,997,999 | A | | 12/1976 | Evans |
| 4,137,353 | A | | 1/1979 | Fariello |
| 4,328,636 | A | * | 5/1982 | Johnson ............ A01K 39/0106 43/107 |
| 4,473,466 | A | * | 9/1984 | Schmidt ............... B07B 1/4609 209/397 |
| 4,903,636 | A | * | 2/1990 | Kroeker ............... A01K 63/003 119/200 |
| 5,108,588 | A | * | 4/1992 | Yu ............... B01D 33/0346 209/237 |
| 5,221,008 | A | * | 6/1993 | Derrick, Jr. ........ B01D 33/0376 209/269 |
| 5,873,327 | A | | 2/1999 | Holyoak |
| 6,474,259 | B1 | * | 11/2002 | Gaugler ............... A01K 67/033 119/6.7 |
| 6,708,443 | B2 | | 3/2004 | Hall |
| 6,990,768 | B1 | * | 1/2006 | Boston ............... A01M 1/02 119/69.5 |
| 7,810,649 | B2 | * | 10/2010 | Robertson ............ B07B 1/4672 209/401 |
| 7,861,866 | B1 | * | 1/2011 | Ondrias ............... B07B 1/54 209/382 |
| 7,867,396 | B2 | * | 1/2011 | Hill ............ C02F 3/04 210/150 |
| 8,025,027 | B1 | | 9/2011 | Morales-Ramos et al. |
| 8,109,035 | B2 | * | 2/2012 | Bowden ............... A01M 1/106 43/107 |
| 8,517,180 | B2 | * | 8/2013 | Raichle ............... B01J 8/0015 209/235 |
| 8,844,465 | B2 | | 9/2014 | Holland et al. |
| 9,010,539 | B2 | * | 4/2015 | Lipa ............... B07B 1/4618 209/392 |
| 9,180,464 | B2 | | 11/2015 | Nimmo et al. |
| 9,265,247 | B2 | * | 2/2016 | Gaugler ............... A01N 25/00 |
| 9,855,518 | B2 | | 1/2018 | Cornelison et al. |
| 9,884,344 | B2 | * | 2/2018 | Wojciechowski ........ B07B 1/46 |
| 9,992,983 | B1 | | 6/2018 | Sobecki et al. |
| 10,251,380 | B2 | * | 4/2019 | Sobecki ............... B07B 1/55 |
| 10,259,012 | B2 | * | 4/2019 | Robertson ............ B07B 1/4663 |
| 10,342,222 | B2 | * | 7/2019 | Sobecki ............... B07B 1/469 |
| 10,450,238 | B2 | * | 10/2019 | Caesar ............... C05F 17/0258 |
| 2002/0184982 | A1 | | 12/2002 | Smith et al. |
| 2004/0206671 | A1 | | 10/2004 | Stichert |
| 2010/0018910 | A1 | * | 1/2010 | Ballman ............... B07B 1/46 209/341 |
| 2013/0277282 | A1 | * | 10/2013 | Lipa ............... B07B 1/4609 209/392 |
| 2014/0166307 | A1 | * | 6/2014 | Cady ............... E21B 21/063 166/378 |
| 2015/0008163 | A1 | | 1/2015 | Nimmo et al. |
| 2015/0183658 | A1 | | 7/2015 | Wright et al. |
| 2017/0042131 | A1 | | 2/2017 | Unger |
| 2018/0077912 | A1 | | 3/2018 | Comparat et al. |
| 2018/0236491 | A1 | | 8/2018 | Gold |

FOREIGN PATENT DOCUMENTS

| | | |
|---|---|---|
| CN | 203692226 | 7/2014 |
| CN | 204232011 | 4/2015 |
| CN | 204232124 | 4/2015 |
| CN | 208853213 | 5/2019 |
| KR | 101372332 | 3/2014 |
| WO | 03007710 | 1/2003 |
| WO | 2016024164 | 2/2016 |

OTHER PUBLICATIONS

U.S. Appl. No. 15/945,851, "Notice of Allowance", dated Nov. 27, 2018, 12 pages.

U.S. Appl. No. 15/945,851, "Supplemental Notice of Allowance", dated Dec. 20, 2018, 2 pages.

Chinese Application No. 201820397471.4, "Office Action", dated Nov. 6, 2018, 4 pages.

Chinese Application No. 201820400218.X, "Office Action", dated Nov. 21, 2018, 3 pages.

"First Research Co-Origination Meeting, Joint FAO/IAEA Division of Nuclear Techniques in Food and Agriculture", Co-ordinated Research Programme on Explore mechanical, molecular, behavioural or genetic methods of sex separation in mosquitoes, Sep. 30-Oct. 4, 2013.

U.S. Appl. No. 15/467,152, "Notice of Allowance", dated Mar. 29, 2018, 11 pages.

Bellini et al., "Use of the sterile insect technique against Aedes albopictus in Italy: first results of a pilot trial", Area-Wide Control of Insect Pests. Springer Netherlands, 2007. 505-515.

Endecotts, "Test sieves—all signed and international standards—Endecotts", (http://www.endecotts.com/products/sieves/), downloaded Jan. 17, 2017.

Hock, "Improved Separator for the Developmental Stages, Sexes, and Species of Mosquitoes", John W. Hock Company, Model 5412 Instructions (http://johnwhock.com/products/laboratory-equipment/larval-pupal-separator/), Copyright 2000-2017.

Mikery-Pacheco et al., "Efficiency of the separation of Aedes (Stegomyia) albopictus (Diptera: Culicidae) male and female pupae using a sieving device", Acta Zoológica Mexicana 31.1 (2015).

U.S. Appl. No. 15/945,851, "Notice of Allowance", dated Sep. 12, 2018, 14 pages.

PCT/US2018/022687, "International Preliminary Report on Patentability", dated Oct. 3, 2019, 11 pages.

SG10201802345X, "Further Written Opinion", dated Aug. 26, 2019, 3 pages.

U.S. Appl. No. 15/467,145, "Corrected Notice of Allowability", dated May 22, 2019, 3 pages.

U.S. Appl. No. 15/467,145, "Notice of Allowance", dated Feb. 13, 2019, 6 pages.

U.S. Appl. No. 16/269,451, "Notice of Allowance", dated Aug. 5, 2019, 10 pages.

CN201820397471.4, "Notice of Decision to Grant", dated Feb. 12, 2019, 2 pages.

CN201820400218.X, "Notice of Decision to Grant", dated Mar. 1, 2019, 2 pages.

SG10201802345X, "Written Opinion", dated Mar. 25, 2019, 8 pages.

Singapore Application No. SG10201802345X, "Notice of Decision to Grant", dated Nov. 6, 2019, 6 pages.

U.S. Appl. No. 15/467,145, "Non Final Office Action", dated Jun. 25, 2018, 13 Pages.

PCT/US2018/022687, "Invitation to Pay Add'l Fees and Partial Search Rpt", dated May 31, 2018, 2 pages.

PCT/US2018/022687, "International Search Report and Written Opinion", dated Jul. 26, 2018, 14 pages.

PCT/US2018/022690, "Invitation to Pay Add'l Fees and Partial Search Rpt", dated May 31, 2018, 2 pages.

PCT/US2018/022690, "International Search Report and Written Opinion", dated Aug. 1, 2018, 15 pages.

U.S. Appl. No. 16/117,758, "Non-Final Office Action", dated Mar. 25, 2020, 13 pages.

(56) References Cited

OTHER PUBLICATIONS

U.S. Appl. No. 16/154,656, "Notice of Allowance", dated Apr. 8, 2020, 11 pages.
U.S. Appl. No. 16/117,758, Notice of Allowance, dated Jul. 20, 2020, 8 pages.
Chinese Application No. 201810243591.3, Office Action, dated Aug. 19, 2020, 12 pages.

* cited by examiner

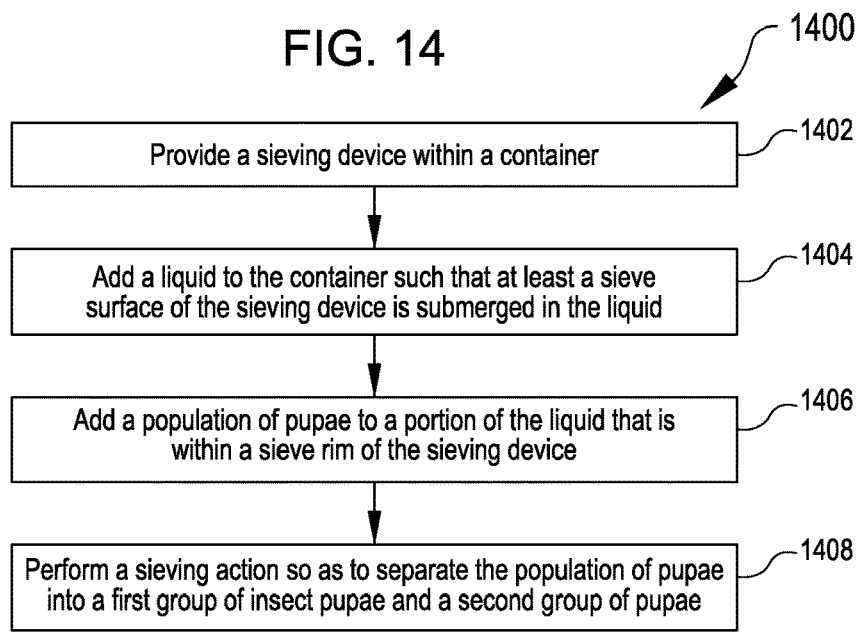
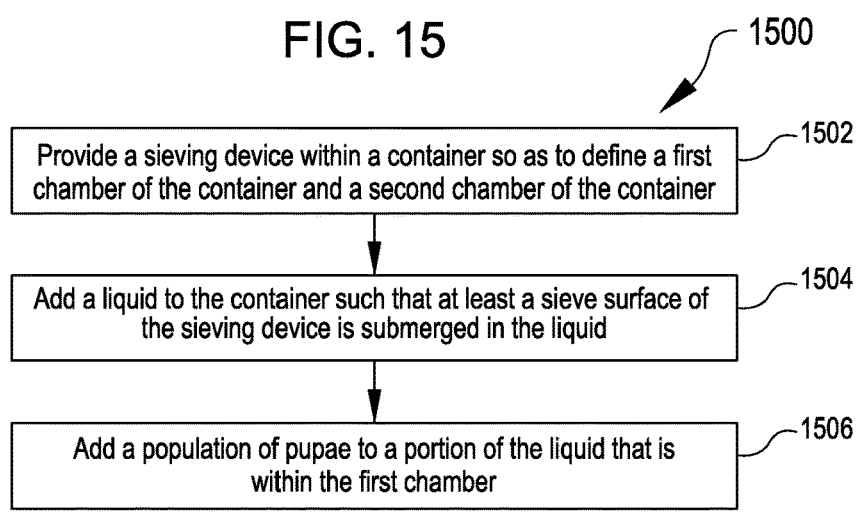
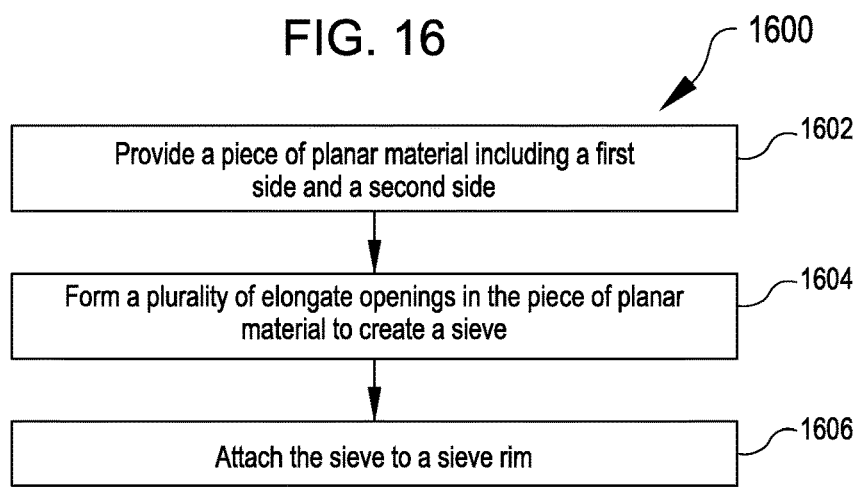

SIEVING DEVICES FOR PUPAE SEPARATION

CROSS REFERENCE TO RELATED APPLICATION

The present application is a division of U.S. patent application Ser. No. 15/467,145, entitled "Sieving Devices For Pupae Separation," filed Mar. 23, 2017, which is incorporated by reference in its entirety herein.

BACKGROUND

Generally, a sieve can be formed of a wire or plastic mesh held in a frame. The sieve can be used for straining solids from liquid or for separating coarser objects from finer objects.

Among those objects that can be separated are insects. Other devices shave been designed to separate insects such as a device that includes parallel glass plates. The reasons for separating insects are various. For example, as part of a Sterile Insect Technique (SIT) program, male insects may be separated from female insects. Depending on the program, separation may be performed at one or more stages of insect development. For example, insects having an aqueous pupal stage may be separated while in the pupal stage.

Use of conventional mesh screens to separate pupae may create challenges given the physiological structures of the pupae. Additionally, use of devices including parallel glass plates may create challenges given their difficulty to operate, high cost, and lack of portability. These challenges may result in prohibitively low throughput and similarly low yield.

SUMMARY

Various examples are described relating to sieving devices, systems including the sieving devices, methods for using the sieving devices, and methods for forming the sieving devices.

In an example, a device is described. The device includes a sieve surface including a first side and a second side. A set of openings is formed in the sieve surface so as to define a set of pathways extending between the first side and the second side. Individual openings of the set of openings are defined by a length dimension measured along a longitudinal axis of a respective opening and a width dimension measured along a transverse axis of the respective opening. The length dimension is greater than the width dimension. The device also includes a sieve rim including a set of walls joined together to create a perimeter of the sieve rim and to define an interior volume. The sieve surface is attached to the sieve rim with the first side of the sieve surface exposed to the interior volume. A value of the width dimension is between 800 microns and 1500 microns, and a value of the length dimension is greater than the value of the width dimension.

In another example, a system is described. The system includes a sieving device and a container. The sieving device includes a sieve rim and a sieve surface attached to the sieve rim. The sieve surface includes a first side and a second side. A set of openings is formed in the sieve surface so as to define a set of pathways extending between the first side and the second side. Individual openings of the set of openings are defined by a length dimension measured along a longitudinal axis of a respective opening, and a width dimension measured along a transverse axis of the respective opening. The container includes at least one wall and a bottom. The at least one wall is attached to the bottom so as to define an opening opposite the bottom. The container is sized to receive the sieve rim and hold a volume of liquid. A value of the width dimension is between 800 microns and 1500 microns, and a value of the length dimension is greater than the value of the width dimension.

In yet another example, a method is described. The method includes providing a sieving device within a container. The sieving device includes a sieve surface in which is formed a plurality of elongate openings. A width dimension of at least one of the elongate openings corresponds to a cephalothorax width of a pupa. The sieving device also includes a sieve rim including a set of walls joined together to create a perimeter of the sieve rim and to define an interior volume. The sieve surface is attached to the sieve rim with a first side of the sieve surface exposed to the interior volume. The method also includes adding a liquid to the container such that at least the sieve surface is submerged in the liquid. The method also includes adding a population of pupae to the liquid that is within the interior volume of the sieve rim. The method also includes performing a sieving action so as to separate the population of pupae into a first group of pupae and a second group of pupae.

In yet another example, a method is described. The method includes providing a sieving device within a container so as to define a first chamber of the container and a second chamber of the container. The sieving device includes a sieve frame and a sieve surface. An exterior surface of the sieve frame engages with an interior surface of the container when the sieving device is provided within the container. The sieve surface is attached to the sieve frame and includes a first side and a second side. A set of elongate openings is formed in the sieve surface so as to define a set of pathways extending between the first side and the second side. The method also includes adding a liquid to the container such that at least the sieve surface is submerged in the liquid. The method also includes adding a population of pupae to a portion of the liquid that is within the first chamber. The method also includes allowing the population of pupae to migrate from the first chamber to the second chamber.

In yet another example, a method is described. The method includes providing a piece of planar material including a first side and a second side. The method also includes forming a plurality of elongate openings in the piece of planar material to create a sieve. Individual elongate openings of the plurality of elongate openings are defined by a length dimension measured along a longitudinal axis of the respective elongate opening, and a width dimension measured along a transverse axis of the respective elongate opening. A value of the width dimension is between 800 microns and 1500 microns, and a value of the length dimension is at least two times greater than the value of the width dimension. The method also includes attaching the sieve to a sieve rim.

The illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one

FIG. 14 illustrates an example process for separating a population of pupae based on size, according to at least one example.

FIG. 15 illustrates an example process for separating a population of pupae based on size, according to at least one example.

FIG. 16 illustrates an example process for manufacturing a sieving device, according to at least one example.

DETAILED DESCRIPTION

Figure 1:
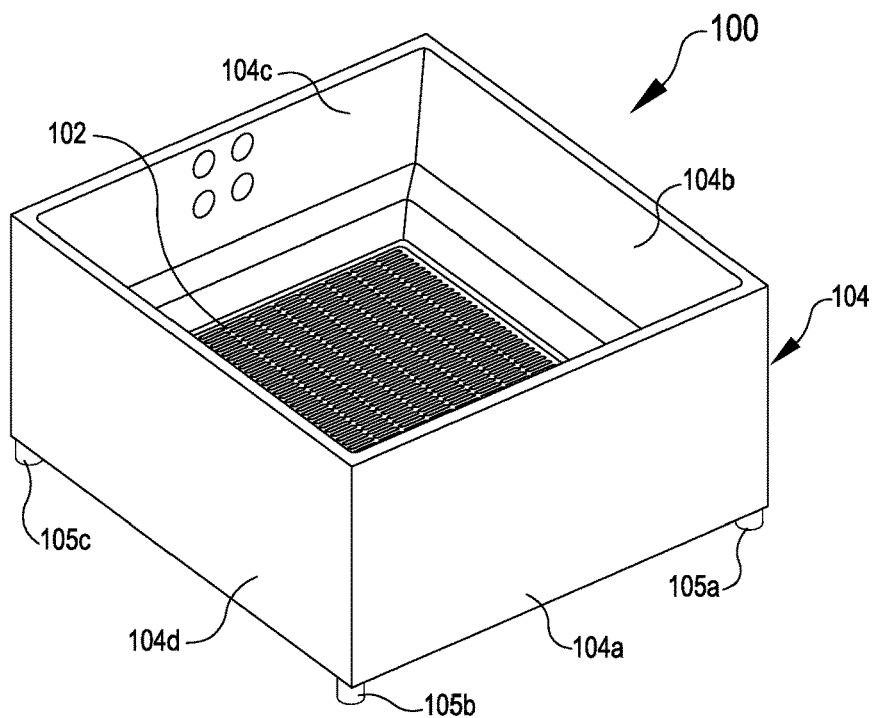
FIG. 1 illustrates a perspective view of a sieving device, according to at least one example.

Examples are described herein in the context of sieving devices for use in separation of mosquito pupae. Those of ordinary skill in the art will realize that the following description is illustrative only and is not intended to be in any way limiting. For example, the sieving devices described herein can be used to separate any insects having an aqueous pupal stage. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a sieving device for separation of pupae is described. The sieving device includes a sieve held within a rim. Together the sieve and the rim from a box-like structure, with the sieve forming the bottom of the box-like structure. The sieve can be a flat plate. A series of repeating elongate openings is formed in the plate. The series of elongate openings cover the entire area of the plate and constitute pathways through which water and certain pupae move. Each elongate opening is defined by a length corresponding to a longitudinal axis and a width corresponding to a transverse axis. The length is greater than the width which results in the openings being described as elongate. A value of the width is selected to correspond to a smallest dimension of a cephalothorax of a typical pupa to be separated. For example, to separate male pupae from female pupae, a value of the width can be selected that is smaller than the cephalothoraxes of most females of a given population and larger than the cephalothoraxes of most males of the same population. To begin separation, the sieving device can be lowered into a container of water at least until the sieve is submerged in the water. The population including males and females can be added the rim of the sieving device (e.g., within the box-like structure). The sieving device can then be dunked into and out of the water to draw the pupae down onto the sieve. Using this action, most, if not all, of the male pupae can pass through any one of the elongate openings, while all of the female pupae are prevented from passing because of their larger cephalothoraxes. The elongate shape of the openings closely corresponds to how the pupae naturally orient in still water. When the water is drained through the elongate openings, those pupae already in this natural orientation remain so and those that are not are oriented by the flowing water. Sizing the elongate openings to correspond to the size and natural orientation of the pupae forces the pupae to be on a single axis of orientation to pass through the sieve. This sizing also results in high separation rates. Additionally, high separation rates are possible because, unlike mesh sieves, the sieve surface is designed to include smooth transitions between the elongate openings. This results in fewer pupae becoming entangled, e.g., by their paddles or other physiological structures, with the openings.

This illustrative example is given to introduce the reader to the general subject matter discussed herein and the disclosure is not limited to this example. The following sections describe various additional non-limiting examples of sieving devices.

Referring now to FIG. 1, FIG. 1 illustrates a perspective view of a sieving device 100, according to at least one example. The sieving device 100 includes a sieve surface 102 held within a sieve rim 104. The sieve rim 104 includes a plurality of walls 104a-104d that together define a volume having a rectangular cross section. In some examples, the sieve rim 104 has a non-rectangular perimeter (e.g., round, triangular, and any other suitable non-rectangular shape). The height of the walls 104 can range between 2-5". In some examples, the height of the walls 104 is greater than 5". Irrespective of the cross section and the wall height, the sieve rim 104 can function to funnel or otherwise direct a liquid (e.g., water) through the sieve surface 102. As the sieving device 100 can be sized for manual use (e.g., 6"×6" square), the sieve rim 104 also provides an area whereby an human operator can manually manipulate the sieving device 100. For example, the operator can use her hands to grasp the sieve rim 104 to manipulate the sieving device 100 (e.g., dunking the sieve surface 102 into and out of a water container to separate pupae). In some examples, the sieving device 100 is manipulated by an automated operator (e.g., an actuator that dunks the sieve surface 102). The sieving device 100 also includes a set of feet 105. The feet 105 are attached to the sieve rim 104 and can function to space the sieve surface 102 of off a bottom of a container or other surface. The sieve surface 102 also includes a series of openings 106 which are described in detail with reference to later figures.

Figure 2:
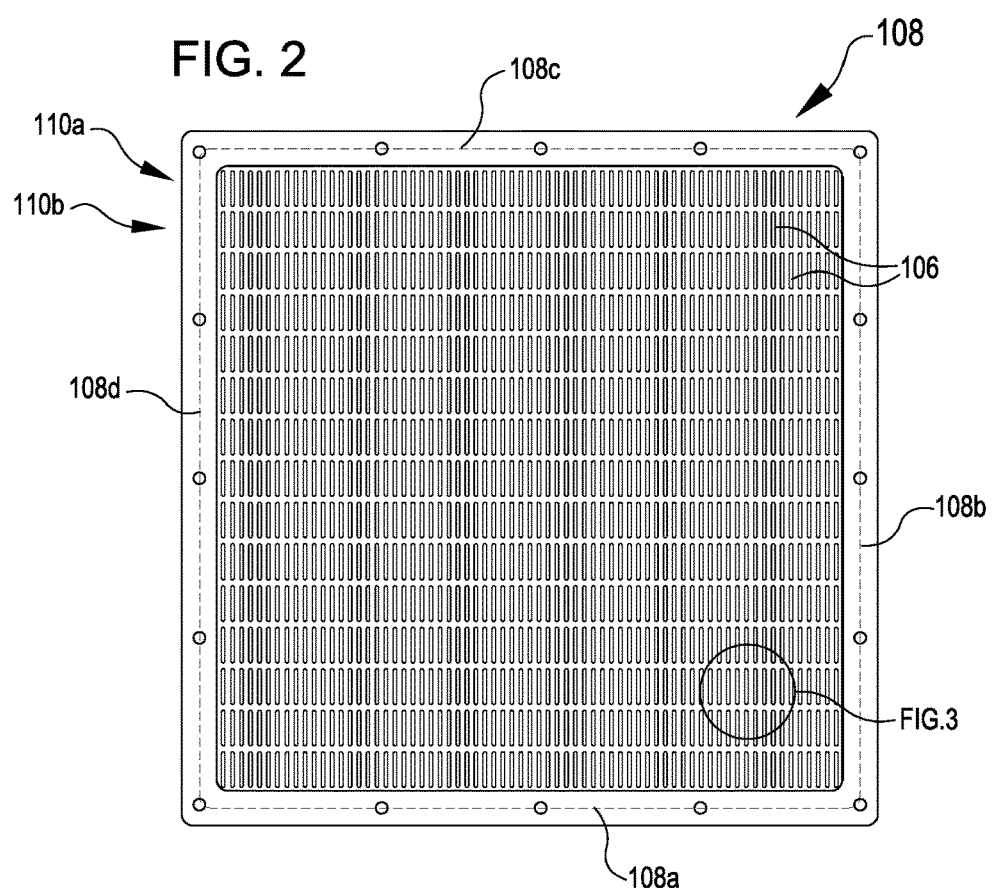
FIG. 2 illustrates a top view of a sieve surface, according to at least one example.

FIG. 2 illustrates a top view of the sieve surface 102, according to at least one example. As illustrated in FIG. 2, the sieve surface 102 can be held within a sieve frame 108. The sieve frame 108 includes a plurality of members 108a-108d that together define a rectangular cross section. In some examples, the sieve frame 108 has a non-rectangular cross section. In any event, the cross section of the sieve rim 104 and the cross section of the sieve frame 108 can correspond to enable mounting of the sieve frame 108 within the sieve rim 104. The sieve frame 108 also provides rigidity to the sieve surface 102. In some examples, sieve frames 108 having different sieve surfaces 102 (e.g., different sized openings) can be detachably mounted to the same sieve rim 104, depending on the implementation. For example, a kit can include multiple sieve surfaces 102 having different sized openings 106 that can be independently detachably mounted to the sieve rim 104. In some examples, more than one sieve surfaces 102 can be held within the sieve frame 108 at any one time. For example, multiple sieve surfaces 102 having different sized openings 106 can be mounted in the sieve frame 104 so as to separate a population of pupae into more than two groups.

As illustrated in FIG. 2, the openings 106 can be organized into a series of rows 110a-110N including a plurality of openings 106. A few of the rows are labeled (e.g., 110a and 110b). The openings 106 can be repeated within the rows 110 to form a row pattern. The rows 110 can be repeated within the sieve surface 102 to form a sieve surface pattern. The number and dimensions of the rows 110 can be a product of the dimensions of the openings 106, spacing between the openings 106, and the material used to form the sieve surface 102. In some examples, a single row 110 including a plurality of openings 106 is provided. In this example, the single row 110 can extend transversely between members 108b and 108d. The openings 106 of this single row 110 can extend longitudinally between members 108a and 108c.

In some examples, the sieve surface 102 is formed by a plurality of elongate rods laid out between the members 110b and 110d. The ends of these rods can extend between the members 108a and 108c and be held in place by these members 108a and 108c. In this example, the openings 106 can be formed between individual ones of the plurality of elongate rods.

Figure 3:
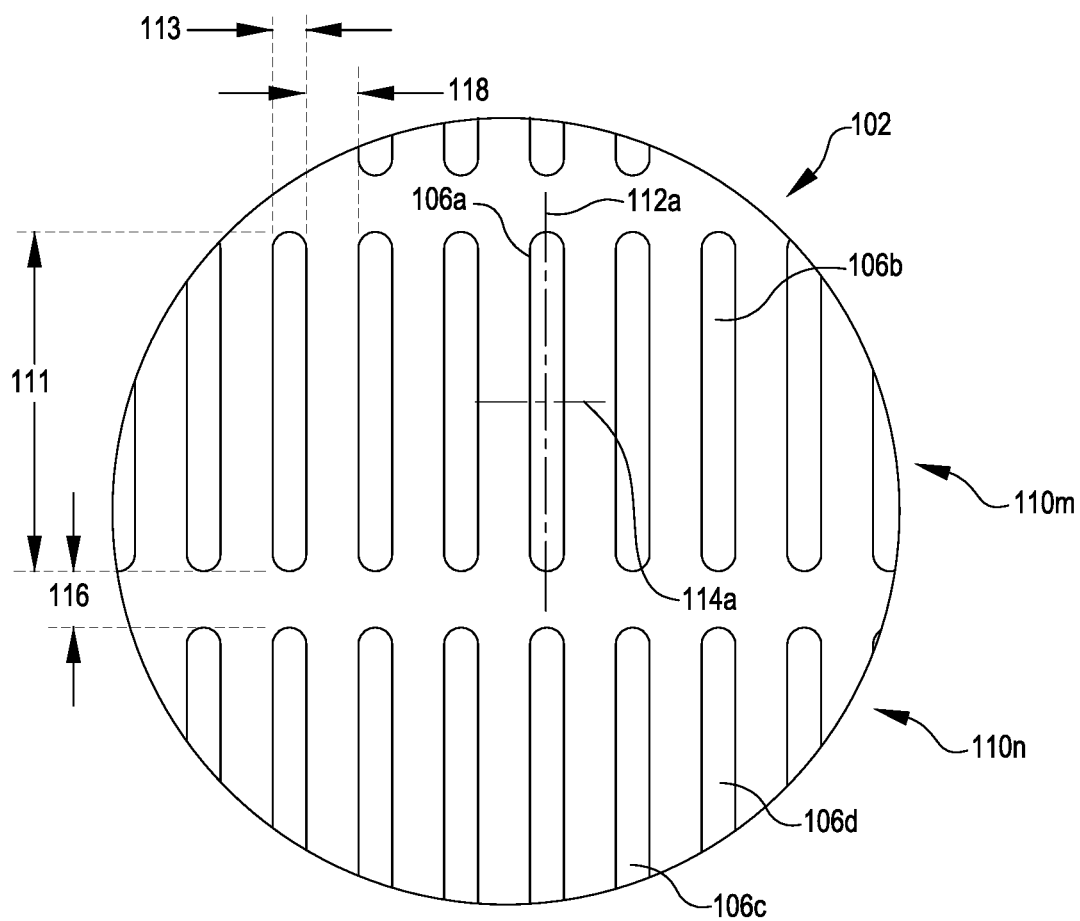
FIG. 3 illustrates a detailed view of the sieve surface from FIG. 2, according to at least one example.

FIG. 3 illustrates a detailed view of the sieve surface 102, according to at least one example. The sieve surface 102 can be defined as having the openings 106, a few of which are labeled. Each opening 106 can have a generally elongate cross section. For example, as illustrated with respect to opening 106a, the cross section can be defined by a length dimension 111 measured along a longitudinal axis 112a of the opening 106a and a width dimension 113 measured along a transverse axis 114a of the opening 106a. The length dimension 111 can be greater than the width dimension 113. As described in detail herein, a generally elongate cross section can enable selection of a smaller width dimension 113 corresponding to the smallest dimension of cephalothorax as compared to square mesh sieves, which are generally sized to the largest dimension of the cephalothorax.

A value of the width dimension 113 can be dependent on the goals of a separation program and characteristics of pupae to be separated. For example, populations of *Aedes aegypti* or *Aedes albopictus* mosquitos can be separated. As described herein, the sieving device 100 can be used to separate any species of insect that has an aquatic pupal phase. In some examples, the value of the width dimension 113 may range from 800 microns to 1500 microns, which may be appropriate for separating mosquitos. Values larger than 1500 microns and smaller than 800 microns may be appropriate for other insect species. In a particular example, the value of the width dimension 113 can be about 1200 microns. A value of the length dimension 111 can also be dependent on the goals of the separation program and characteristics of the pupae to be separated. For example, the value of the length dimension 111 may range from 2500 microns to many millimeters (e.g., 12 millimeters). For example, in the example illustrated in FIG. 3, the value of the length dimension 111 is about 10 times greater than the value of the width dimension 113. In some examples, the value of the length dimension 111 can be arbitrarily selected so long as it is greater than a largest cross-sectional dimension (e.g., tip to tail) of a typical pupa which is expected to pass through the opening 106a. Because the width dimension 113 is sized to correspond to a different smaller dimension of the typical pupa, the length dimension 111 will be larger than the width dimension 113.

The rows 110 can be spaced in accordance with a row dimension 116. For example, row 110m including the openings 106a, 106b can be spaced apart from row 110n including the openings 106c, 106d by the row dimension 116. A value of the row dimension 116 may range from 1000 microns to 3000 microns. In some examples, the value of the row dimension 116 is much greater than 3000 microns. The openings 106 can be spaced in accordance with a space dimension 118. For example, the opening 106a can be spaced apart from the opening 106b by the space dimension 118. A value of the space dimension 118 may range from about 500 microns to 3000 microns. In some examples, the value of the space dimension 118 is much greater than 3000 microns. Depending on the value of the row dimension 116, the value of the space dimension 118, the value of the length dimension 111, and the value of the width dimension 113, an example sieve surface 102 may have between 5-30 openings 106 per square inch. In some examples, the value of the row dimension 116, the value of the space dimension 118, the value of the length dimension 111, and the value of the width dimension 113 are selected to provide sufficient rigidity to the sieving device 100 and a suitable fraction of open area to solid structure (e.g., openings 106 compared to rigid portion of the sieve surface 102), while still preventing entanglement with the pupae.

In some examples, the values of the row dimension 116 and the space dimension 118 are selected to minimize a ratio of solid area to open area across the sieve surface 102. Thus, by placing the openings 106 close together (e.g., a small value of the space dimension 118) and placing the rows 110 close together (e.g., small value of the row dimension 116), a greater quantity of openings 106 and rows 110 can be formed in the sieve surface 102. This can provide for increased throughput and increased yield in a separation program.

In some examples, the values of the row dimension 116 and the space dimension 118 depends on the material selected for the sieve surface 102 and the forming method.

The sieve surface 102 can be formed from any suitable material such as metal, plastic, glass, ceramic, acrylic, and other materials having similar properties. The forming technique used to form the sieve surface 102 will depend on the material selected. Example forming techniques include, but are not limited to, laser cutting, water jet cutting, photochemical etching, punching, die cutting, milling, additive manufacturing (e.g., three-dimensional printing), molding, casting, stamping, and other similar techniques.

Figure 4:
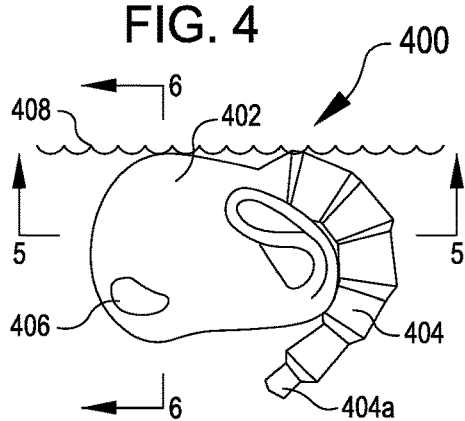
FIG. 4 illustrates a side view of an example mosquito pupa that can be separated using a sieving device as described herein, according to at least one example.
Figure 5:
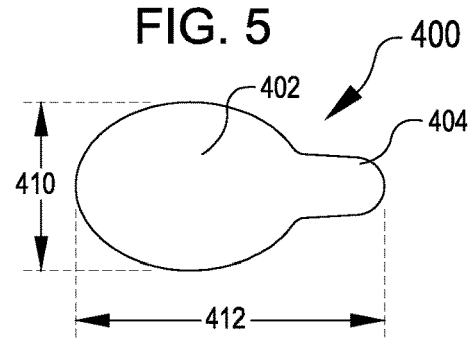
FIG. 5 illustrates a profile view of an example mosquito pupa that can be separated using a sieving device as described herein, according to at least one example.
Figure 6:
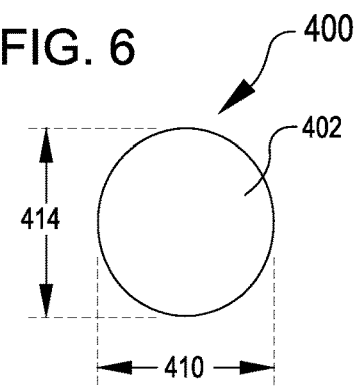
FIG. 6 illustrates a profile view of an example mosquito pupa that can be separated using a sieving device as described herein, according to at least one example.

FIGS. 4, 5, and 6 respectively illustrate a side view, a first profile view, and a second profile view of an example mosquito pupa 400 that can be separated using the sieving device 100, according to various examples. The mosquito pupa 400 includes a cephalothorax 402 and an abdomen 404. When in the pupal stage, the mosquito pupa 400 uses its abdomen 404, including a distal portion 404a, as a flipper to move through water 408. The cephalothorax 402 also includes eyes 406, one of which is illustrated and labeled. In the profile view illustrated in FIG. 5, the mosquito pupa 400 can be defined by a cephalothorax width 410 and an overall length 412. In the profile view illustrated in FIG. 6, the mosquito pupa 400 can also be defined by the cephalothorax height 414. Based on the physiological structures of the pupae (e.g., the mosquito pupa 400), the cephalothorax width 410 will be less than the overall length 412. In some examples, the cephalothorax height 414 is greater than the cephalothorax width 410. Thus, the cephalothorax width 410 can represent the narrowest dimension of the largest part (e.g., the cephalothorax 402) of the mosquito pupa 400.

As introduced herein, the value of the length dimension 111 of the openings 106 can be selected based on the overall length 412. For a given pupal population, a minimum value for the length dimension 111 should be greater than the overall length 412 of the largest pupa in the population. In some examples, a value of the length dimension 111 is much greater the overall length 412 of the largest pupa (e.g., an order of magnitude of 10 to 100 times greater).

As introduced herein, the value of the width dimension 113 of the openings 106 can be selected based on the cephalothorax width 410. For example, assume for a moment that a goal of a separation program is to separate male mosquito pupae from female mosquito pupae. In this example, if an example male population has an average cephalothorax width 410 of 1100 microns and an example female population has an average cephalothorax width 410 of 1400 microns. Given this difference of 300 microns between the average cephalothorax widths and given a difference of about 50 microns between a female mosquito with the smallest cephalothorax width 410 (e.g., 1250 microns) in the female population and a male mosquito pupa with the largest cephalothorax width 410 (e.g., 1200 microns) in the male population, a value for the width dimension 113 can be selected to give a high probability of separation. In this example, a value of 1200-1225 microns for the width dimension 113 can be suitable.

In the view illustrated in FIG. 4, the mosquito pupa 400 is oriented in a natural orientation, one in which the mosquito pupa 400 will naturally orient when located within the water 408. In this orientation, the mosquito pupa 400 is able to obtain oxygen at the surface of the water 408 via respiratory trumpets (not shown) that extend from an upper portion of the cephalothorax 402 (e.g., near the upper surface of the water 408). This orientation may be referred to as a "tail-down orientation" because the distal portion 404a of the abdomen 404 (e.g., a tail) points down.

Figure 7:
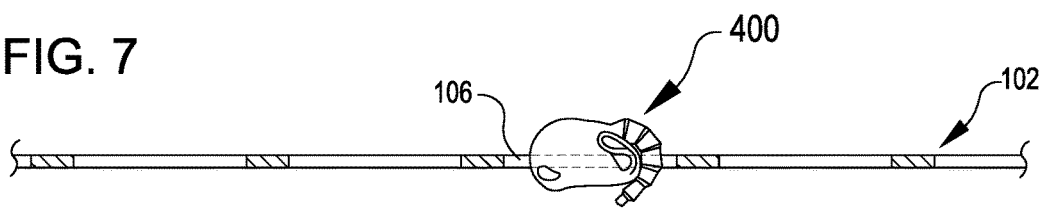
FIG. 7 illustrates a side view of a mosquito pupa passing through an opening of a sieve surface, according to at least one example.

FIG. 7 illustrates a side view of the mosquito pupa 400 passing through the opening 106 in the sieve surface 102, according to at least one example. In the example illustrated in FIG. 7, the mosquito pupa 400 is oriented in the tail-down orientation as the mosquito pupa 400 passes through the opening 106.

Figure 8:
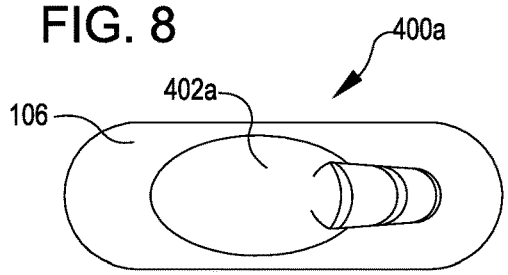
FIG. 8 illustrates a mosquito pupa aligned in a first orientation with respect an opening of a sieve surface, according to at least one example.
Figure 9:
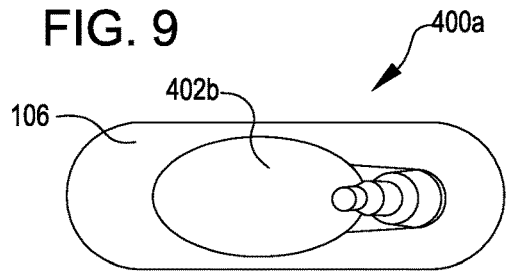
FIG. 9 illustrates a mosquito pupa aligned in a second orientation with respect an opening of a sieve surface, according to at least one example.

FIGS. 8 and 9 respectively illustrate a first mosquito pupa 400a in a first orientation and a second orientation with respect an opening 106, according to various examples. In particular, the first mosquito pupa 400a is shown passing through the opening 106. This is because the cephalothorax width 410 of a first cephalothorax 402a is less than a value of the width dimension 113. The first orientation of the first mosquito pupa 400a illustrated in FIG. 8 is an example of the tail-down orientation illustrated in FIGS. 4 and 7. The second orientation of the first mosquito pupa 400a illustrated in FIG. 9 is an example of a tail-up orientation. This may constitute a rotation of about 180 degrees.

Figure 10:
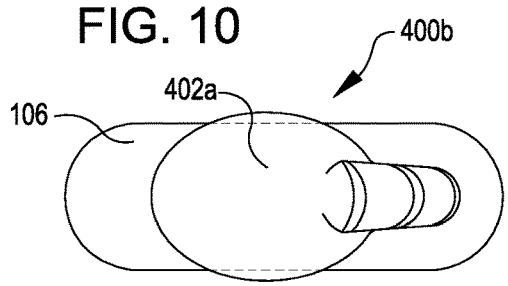
FIG. 10 illustrates a mosquito pupa aligned in a first orientation with respect an opening of a sieve surface, according to at least one example.
Figure 11:
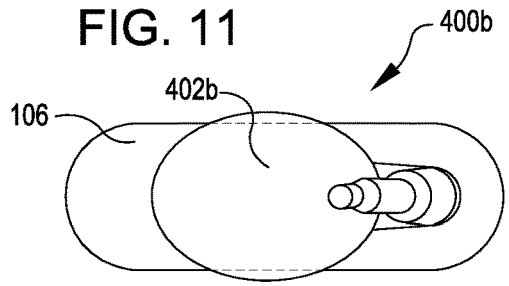
FIG. 11 illustrates a mosquito pupa aligned in a second orientation with respect an opening of a sieve surface, according to at least one example.

FIGS. 10 and 11 respectively illustrate a second mosquito pupa 400b in a first orientation and a second orientation with respect an opening 106, according to various examples. In particular, the second mosquito pupa 400b is shown as being prevented from passing the opening 106. This is because the cephalothorax width 410 of a second cephalothorax 402b is greater than a value of the width dimension 113. The first orientation of the second mosquito pupa 400b illustrated in FIG. 10 is an example of the tail-down orientation illustrated in FIGS. 4 and 7. The second orientation of the second mosquito pupa 400b illustrated in FIG. 11 is an example of the tail-up orientation. This may constitute a rotation of about 180 degrees.

In some examples, the openings 106 of the sieve surface 102 are sized such that the first mosquito pupae 400a can pass through the openings 106 and the second mosquito pupae 400b are prevented from passing through the openings 106. For example, the first mosquito pupae 400a may be male pupae and the second mosquito pupae 400b may be female pupae. In some examples, the first mosquito pupae 400a is a first set of male (or female) pupae and the second mosquito pupae 400b is a second set of male (or female) pupae.

In some examples, the openings 106 of the sieve surface 102 are sized such that the first mosquito pupae 400a can pass through the openings 106 in any one of the tail-down or tail-up orientations and the second mosquito pupae 400b are prevented from passing through in any orientation. In some examples, the openings 106 are sized such that the first mosquito pupae 400a may pass through in other orientations as well (e.g., head down or abdomen down).

Figure 12:
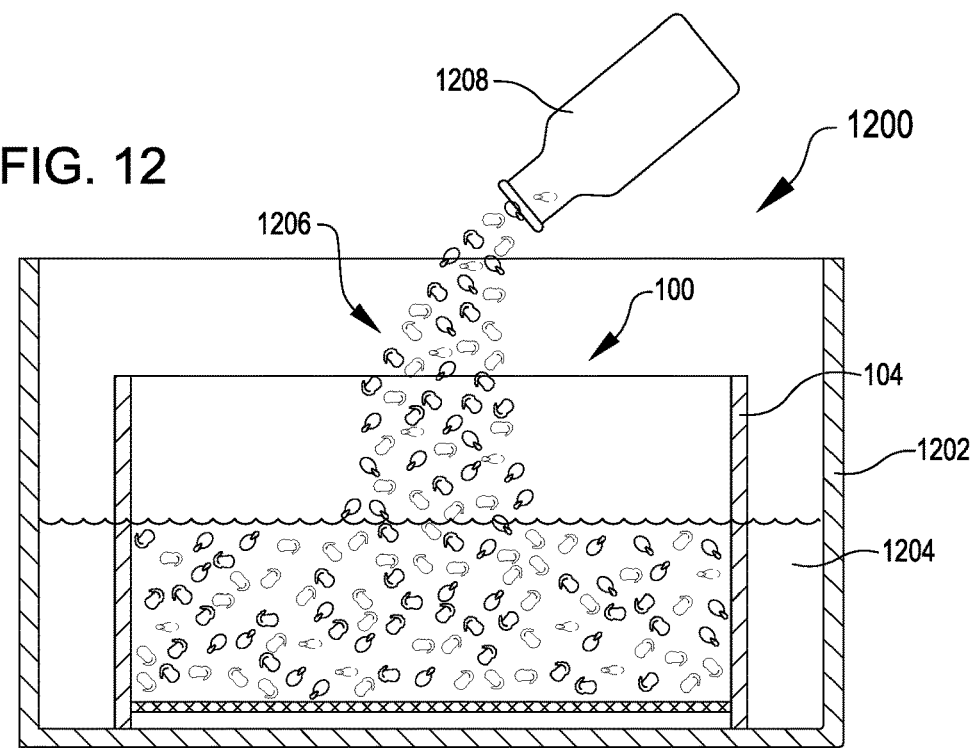
FIG. 12 illustrates a first state of an example system for separating a population of pupae, according to at least one example.
Figure 13:
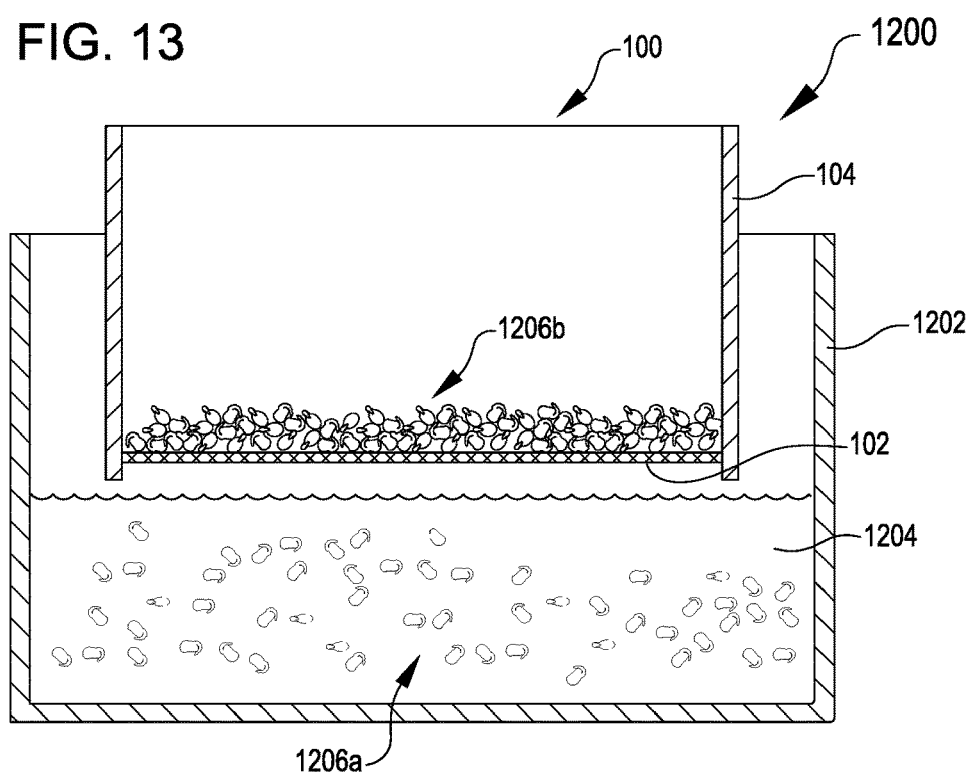
FIG. 13 illustrates a second state of the example system of FIG. 12, according to at least one example.

FIGS. 12 and 13 illustrate states of an example system 1200 for separating a population of pupae into a first group and a second group, according various examples. The system 1200 includes the sieving device 100 and a container 1202. The container 1202 can be any suitable container capable of holding a liquid 1204 and sized to receive the sieving device 100. The container 1202 can have any suitable cross sectional shape such as rectangular, circular, and any other non-rectangular shape. The liquid 1204 can be water or some other similar liquid.

As illustrated in FIG. 12, the sieving device 100 has been placed inside the container 1202 and the liquid 1204 has been added to the container 1202. In some examples, the liquid 1204 is added after the sieving device 100 has been placed in the container 1202. In any event, the sieve surface 102 can be submerged in the liquid 1204. As also illustrated in FIG. 12, a population of pupae 1206 is being added to the liquid 1204. In particular, the population of pupae 1206 is being poured from a pupae container 1208 and into a portion of the liquid 1204 that is inside the sieve rim 104. In this manner, the population of pupae 1206 land on the surface of the liquid 1204 as opposed to landing on the sieve surface 102.

In some examples, the population of pupae 1206 have been previously raised within a lab, captured in the wild, or otherwise acquired. The population of pupae 1206 can include pupae having varied characteristics. For example, the population of pupae 1206 can include pupae of various sexes, of various sizes, of various species, and the like.

As illustrated in FIG. 13, the sieving device 100 can be raised vertically so as to remove the sieve surface 102 from the liquid 1204. In some examples, this action constitutes a sieving action which causes the population of pupae 1206 to be drawn down towards the sieve surface 102 as the liquid 1204 drains through openings (e.g., the openings 106) of the sieve surface 102 (e.g., out of the sieve rim 104) and back into the container 1202. Repeating this sieving action one or more times may cause the population of pupae 1206 to separate into a first pupa group 1206a and a second group of pupae 1206b. The first group of pupae 1206a may be those pupae of the population 1206 that are small enough to pass through the openings 106 of the sieve surface 102. For example, the first group of pupae 1206a may include male pupae. The second group of pupae 1206b may be those pupae of the population 1206 that are too large to pass through the openings 106 of the sieve surface 102. For example, the second group of pupae 1206b may include female pupae.

In the example illustrated in FIG. 13, the sieving action includes changing an elevation of the sieve surface 102 with respect to the liquid 1204 (e.g., dunking the sieving device 100 into and out of the liquid 1204). In some examples, the sieving action includes changing a level of the liquid 1204 with respect to the sieve surface 102. For example, the liquid 1204 can be drained from the container 1202 and recirculated into the container 1202. In some examples, the liquid 1204 is drained from the container 1202 and new liquid is added to the container 1202.

Once the sieving action has been performed a suitable number of times, the sieving device 100 can be removed from the container 1202 and the second group of pupae 1206b can be captured from the sieving device 100 or otherwise disposed of. For example, the sieving device 100 can be inverted and the second group of pupae can be collected from the sieving device 100. The liquid 1204 can be poured out of the container 1202 along with the first group of pupae 1206a so as to capture the first group of pupae 1206a. In some examples, the liquid 1204 is poured through a finer sieve or filter usable to capture the first group of pupae 1206a. Once separated, the two groups of pupae 1206a, 1206b can be processed and used for any suitable purpose.

In some examples, use of the system 1200 enables quick separation of pupae with high yield rates as compared to conventional techniques. For example, 5000 mosquito pupae can be separated based on size in about thirty seconds.

In some examples, the system 1200 can be used for separating the first group of pupae 1206a and the second group of pupae 1206b into one or more subgroups. For example, sieving devices 100 having sieve surfaces 102 with differently sized openings 106 can be used in sequence to further refine the separation of the pupae. For example, the second group of pupae 1206b which did not pass through the first sieve surface 102 can be sieved again using a sieve surface with larger openings than the first surface 102. The sieving process can be repeated to sort precisely by size differential. This process can also be performed in reverse, where the largest sieve surface 102 is used first, and sequentially moving to smaller and smaller sieve surfaces 102.

In some examples, the sieve surface 102 is used in a mostly passive process of separating a population of pupae based on size (e.g., without performing a sieving action). For example, in the sieve surface 102, within the sieve frame 108 or otherwise, can be sized to index within a container. For example, an exterior surface of the sieve surface 102 can be sized to engage with an interior surface of the container. The sieve surface 102 can be placed within the container so as to define two chambers. This may create a seal between the between the sieve surface 102 and the container such that, to pass between the two chambers, pupae must pass through the sieve surface 102.

In this example, the container can have a bottom, sides, and an opening opposite the bottom. The sieve surface 102 can be placed to have a vertical orientation within the container. For example, if the sieve surface 102 and the container have square cross sections, in the vertical orientation, a first edge of the sieve surface 102 can contact the bottom of the container and two edges of the sieve surface 102 can contact two opposing walls of the container. The sieve surface 102 can also be placed to have a horizontal orientation within the container. For example, if the sieve surface 102 and the container have square cross sections, in the horizontal orientation, a two opposite edges of the sieve surface 102 can contact two opposing walls of the container and the other two opposite edges of the sieve surface 102 can contact the other two opposing walls of the container.

Continuing with this example, pupae can be added to one of the two chambers. For example, in the horizontal orientation, the pupae can be added along with a first volume of water before the sieve surface 102 is mounted in the container. Afterwards, a second volume of water can be added that submerges the sieve surface and provides an aqueous path for the pupae to pass between the two chambers. Thus, in the horizontal orientation, the pupae can be placed in the lower chamber. In this manner, in order to reach air at the surface, the pupae are required to pass through the sieve surface 102. The instinct to reach the air can cause the pupae to attempt to pass through the sieve surface 102. In some examples, in any orientation, a stimulus can be directed to the pupae that stimulates their movement across the sieve surface 102. For example, sounds, lights, food, and the like may be used to stimulate the pupae.

In some examples, multiple sieve surfaces 102 with different sized openings 106 are installed in series in a single container to create three or more chambers. For example, the sizes of the openings 106 in the respective sieve surfaces 102 can decrease from a first end of the container to a second end. As a population of pupae move from a first chamber nearest the first end toward the second end, the population can be separated into two or more groups based on size, with the size of the pupae decreasing in size from the first chamber toward the second end.

FIG. 14 illustrates an example process 1400 for separating a population of pupae based on size, according to at least one example. The process 1400 can be performed using the system 1200 or any other comparable system.

The process 1400 begins at 1402 by providing a sieving device within a container. The sieving device can include a sieve surface and a sieve rim. In the sieve surface can be formed a plurality of elongate openings. The sieve surface can be attached to the sieve rim. In some examples, the plurality of elongate openings define a plurality of pathways extending between a first side of the sieve surface and a second side of the surface. The elongate openings of the plurality of elongate openings can be defined by a length dimension and a width dimension. The length dimension can be measured along a longitudinal axis of each elongate opening. The width dimension can be measured along a transverse axis of each elongate opening. In some examples, the length dimension is larger than the width dimension. In some examples, a value of the width dimension corresponds to a cross-sectional cephalothorax width of a typical pupa of the first group of pupae.

At 1404, the process 1400 includes adding a liquid to the container such that at least the sieve surface is submerged in the liquid. In some examples, the liquid is water.

At 1406, the process 1400 includes adding a population of pupae to a portion of the liquid that is within the sieve rim of the sieving device. In some examples, the pupae are be disposed within water that is poured into the portion of the liquid. In some examples, the population of pupae are treated with a larvicide prior to being added to the sieving device. This ensures any larvae still present in the population are dead prior to going through the sieving process.

At 1408, the process 1400 includes performing a sieving action so as to separate the population of pupae into a first group of pupae and a second group of pupae.

In some examples, the sieving action includes raising and lowering the sieving device relative to the liquid between: a first elevation at which the sieve surface is submerged in the liquid, and a second elevation at which the sieve surface is removed from the liquid. In some examples, the sieving action is performed as quickly as one cycle per every two seconds (e.g., one second down and one second up). In some examples, the cycle time is determined based on the time it takes for the liquid to drain through the sieve surface and fill the sieve rim. Thus, the cycle time may depend on the open area of the sieve surface and the volume of the sieve rim. In some examples, the cycle time decreases as the sieve surface becomes clogged with pupae (e.g., towards the end of the sieving action).

In some examples, the sieving action includes raising and lowering a level of the liquid relative to the sieve surface between: a first liquid level defined at a first vertical elevation above the sieve surface, and a second liquid level defined at a second vertical elevation below the sieve surface. In some examples, raising and lowering the level of the liquid relative to the sieve surface includes recirculating the liquid between the container and a secondary container. In some examples, raising and lowering the level of the liquid relative to the sieve surface includes removing the liquid from the container and replacing the liquid in the container with different liquid.

In some examples, the process 1400 can further include, after performing the sieving action, removing the sieving device from the container and removing the liquid from the container. The sieving device can contain the second group of pupae. The liquid can contain the first group of pupae. In some examples, the population of pupae includes male pupae and female pupae. The first group of pupae can include a first portion of the male pupae. The second group of pupae can include a second portion of the female pupae.

In some examples, the process 1400 can further include allowing the population of pupae to migrate from the first chamber to the second chamber. As noted, this can include passively allowing the pupae to migrate and/or stimulating the pupae.

FIG. 15 illustrates an example process 1500 for separating a population of pupae based on size, according to at least one example. The process 1500 can be performed using the sieving device 100, with or without the sieve rim 104, disposed within a container such as the container 1202.

The process 1500 begins at 1502 by providing a sieving device within a container so as to define a first chamber of the container and a second chamber of the container. In some examples, the sieving device includes a sieve frame and a sieve surface attached to the sieve frame. An exterior surface of the sieve frame can engage with an interior surface of the container when the sieving device is provided within the container. The sieve surface can be attached to the sieve frame and can include a first side and a second side. A set of elongate openings can be formed in the sieve surface so as to define a set of pathways extending between the first side and the second side.

In some examples, the container includes at least one wall and a bottom. The at least one wall can be attached to the bottom so as to define an opening opposite the bottom. The first chamber can be disposed proximate to the bottom of the container. The second chamber can be disposed proximate to the opening of the container.

In some examples, at least some elongate openings of the set of elongate openings of the sieve surface are defined by a length dimension and a width dimension. The length dimension can be measured along a longitudinal axis of the elongate opening. The width dimension can be measured along a transverse axis of the elongate opening. In some examples, the length dimension is larger than the width dimension.

At 1504, the process 1500 includes adding a liquid to the container such that at least the sieve surface is submerged in the liquid. In some examples, adding the liquid includes adding a first portion of the liquid to the container, and, after adding the population of pupae, adding a second portion of the liquid such that at least the sieve surface is submerged in the second portion liquid.

At 1506, the process 1500 includes adding a population of pupae to a portion of the liquid that is within the first chamber. In some examples, a first group of pupae of the population is free to move between the first chamber and the second chamber via any one of the elongate openings of the sieve surface. In some examples, a second group of pupae of the population is prevented, by sieve surface, from moving from the first chamber to the second chamber.

In some examples, the process 1500 further includes providing a stimulus that stimulates movement of the population of pupae toward the second chamber.

FIG. 16 illustrates an example process 1600 for manufacturing a sieving device such as the sieving device 100, according to at least one example.

The process 1600 begins at 1602 by providing a piece of planar material including a first side and a second side. For example, the piece of planar material can be a sheet of stainless steel, aluminum, steel, titanium, or any other material having planar properties.

At 1604, the process 1600 includes forming a plurality of elongate openings in the piece of planar material to create a sieve. In some examples, each elongate opening of the plurality of elongate openings is defined by a length dimension and a width dimension. The length dimension can be measured along a longitudinal axis of the elongate opening. The width dimension can be measured along a transverse axis of the elongate opening. In some examples, the width dimension is less than the length dimension and is selected to correspond to a cross-sectional cephalothorax width of a pupa.

In some examples, forming the plurality of elongate openings includes forming by at least one of laser cutting, water jet cutting, photochemical etching, or milling.

At 1606, the process 1600 includes attaching the sieve to a sieve rim. In some examples, this includes attaching the sieve to a sieve frame and attaching the sieve frame to the sieve rim. In some examples, attaching the sieve to the sieve rim includes attaching using fasteners, welding, a press-fit, a snap-fit, and any other suitable means for attaching.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

What is claimed is:

1. A sieving container, comprising:
   a base defining a set of openings extending between a first side of the base and a second side of the base, individual openings of the set of openings defined by:
   a length dimension measured along a longitudinal axis of a respective opening, wherein a value of the length dimension is greater than an overall length of a representative insect pupa of a predetermined insect type to be sieved using the sieving container;
   a width dimension measured along a transverse axis of the respective opening, the length dimension greater than the width dimension, wherein a value of the width dimension is less than a cross-sectional cephalothorax width of the representative insect pupa; and
   a space dimension measured between longitudinal edges of the individual openings, wherein a value of the space dimension corresponds the cross-sectional cephalothorax width of the representative insect pupa;
   a sieve frame that encircles the base and physically contacts at least the first side of the base, the base fixedly coupled to the sieve frame; and
   a perimeter wall encircling the base and the sieve frame to form an interior volume of the sieving container, the sieve frame fixedly coupled to the perimeter wall with the first side of the base exposed to the interior volume.

2. The sieving container of claim 1, wherein the value of the length dimension is at least two times greater than the value of the width dimension.

3. The sieving container of claim 1, wherein respective length dimensions of individual openings are parallel.

4. The sieving container of claim 1, wherein the representative insect pupa is a female mosquito pupa.

5. The sieving container of claim 1, wherein the base is formed from a single piece of planar material.

6. The sieving container of claim 1, wherein the base is formed from a plurality of elongate rods held within the sieve frame in a substantially parallel orientation so as to define the set of openings therebetween.

7. The sieving container of claim 1, wherein, when the base is submerged in a liquid:
   a first mosquito pupa of the predetermined insect type having a first cephalothorax width that is less than the value of the width dimension is free to move through any one of the set of openings between the first side and the second side; and
   a second mosquito pupa having a second cephalothorax width that is greater than the value of the width dimension is prevented from moving between any one of the set of openings between the first side and the second side.

8. The sieving container of claim 1, wherein:
   the base is a first base and the set of openings is a first set of openings; and
   the sieving container further comprises a second base comprising a first side and a second side, wherein a second set of openings is formed in the second base, wherein the second base is fixedly coupled to the sieve frame with the first side of the second base exposed to the interior volume and the second side of the second base exposed to the first side of the first base, and wherein openings of the second set of openings are sized differently from openings of the first set of openings.

9. A sieving container, comprising:
   a base comprising a first side and a second side wherein a set of openings is formed in the base so as to define a set of pathways extending between the first side and the second side, individual openings of the set of openings defined by:
   a length dimension measured along a longitudinal axis of a respective opening, wherein a value of the length dimension is greater than an overall length of a representative female mosquito pupa of a population of mosquito pupae to be sieved using the sieving container;
   a width dimension measured along a transverse axis of the respective opening, the length dimension greater than the width dimension, wherein a value of the width dimension is less than a cross-sectional cephalothorax width of the representative female mosquito pupa; and
   a space dimension measured between longitudinal edges of the individual openings, wherein a value of the space dimension corresponds to the cross-sectional cephalothorax width of the representative female mosquito pupa;
   a sieve frame that encircles the base and physically contacts at least the first side of the base, the based fixedly coupled to the sieve frame; and
   a perimeter wall encircling the base and the sieve frame to form an interior volume of the sieving container, the sieve frame fixedly coupled to the perimeter wall, the interior volume configured to receive a liquid.

10. The sieving container of claim 9, wherein sieving the population of mosquito pupae comprises preforming a sieving action to separate the population of mosquito pupae present in a liquid based on cephalothorax width.

11. The sieving container of claim 10, wherein the sieving action comprises raising and lowering the base relative to the liquid between:
 a first elevation at which the base is submerged in the liquid; and
 a second elevation at which the base is removed from the liquid.

12. The sieving container of claim 10, wherein the sieving action comprises raising and lowering a level of the liquid relative to the base between:
 a first liquid level defined at a first vertical elevation above the base; and
 a second liquid level defined at a second vertical elevation below the base.

13. The sieving container of claim 9, further comprising one or more handles connected to the perimeter wall.

14. The sieving container of claim 9, wherein the sieve frame is detachably coupled to the perimeter wall, wherein the perimeter wall is configured to detachably receive a different sieve frame comprising a different base that comprises different openings when the base is detached from the perimeter wall.

15. The sieving container of claim 9, wherein a distribution of the set of openings across the base is between substantially five and substantially thirty openings per square inch.

16. The sieving container of claim 9, wherein
 the value of the space dimension is less than the cross-sectional cephalothorax width of the representative female mosquito pupa.

17. The sieving container of claim 9, wherein the value of the width dimension is between 800 microns and 1500 microns, and the value of the space dimension is between 500 and 3000 microns.

18. A method of forming a sieving container, comprising:
 providing a piece of planar material comprising a first side and a second side;
 forming a plurality of elongate openings in the piece of planar material to create a base, individual elongate openings of the plurality of elongate openings defined by:
  a length dimension measured along a longitudinal axis of the respective elongate opening, wherein a value of the length dimension is greater than an overall length of a representative insect pupa of a predetermined insect type to be sieved using the sieving container;
  a width dimension measured along a transverse axis of the respective elongate opening, wherein a value of the width dimension is less than a cross-sectional cephalothorax width of the representative insect pupa;
  a space dimension measured between longitudinal edges of the individual openings, wherein a value of the space dimension corresponds to the cross-sectional cephalothorax width of the representative insect pupa;
 forming a sieve frame;
 coupling the base to the sieve frame such that the sieve frame encircles the base, and the first side of the base physically contacts the sieve frame;
 forming a perimeter wall; and
 coupling the perimeter wall to the sieve frame such that the perimeter wall encircles the base and the sieve frame to form an interior volume.

19. The method of claim 18, wherein forming the plurality of elongate openings comprises forming by at least one of laser cutting, water jet cutting, photochemical etching, punching, die cutting, or milling.

20. The sieving container of claim 9, wherein the value of the length dimension and the value of the width dimension are selected to:
 prevent male mosquito pupae of the population of mosquito pupae oriented in a first orientation from passing through the set of openings when sieving the population of mosquito pupae; and
 allow the male mosquito pupae of oriented in a second orientation to pass.

* * * * *